United States Patent
Anderson

(10) Patent No.: US 8,639,358 B2
(45) Date of Patent: Jan. 28, 2014

(54) FAIL-SAFE IMPLANTABLE MEDICAL ELECTRICAL LEAD

(75) Inventor: Kenneth Anderson, Bloomington, MN (US)

(73) Assignee: Medtronic, Inc, Minneapolis, MN (US)

( * ) Notice: Subject to any disclaimer, the term of this patent is extended or adjusted under 35 U.S.C. 154(b) by 0 days.

(21) Appl. No.: 13/350,403

(22) Filed: Jan. 13, 2012

(65) Prior Publication Data

US 2013/0184800 A1 Jul. 18, 2013

(51) Int. Cl.
*A61N 1/375* (2006.01)

(52) U.S. Cl.
USPC .............................. 607/122; 607/119; 607/5

(58) Field of Classification Search
USPC ...................................... 607/5, 119
See application file for complete search history.

(56) References Cited

U.S. PATENT DOCUMENTS

| | | | |
|---|---|---|---|
| 4,964,414 A | 10/1990 | Handa et al. | |
| 5,246,014 A | 9/1993 | Williams et al. | |
| 5,534,022 A | 7/1996 | Hoffmann et al. | |
| 5,676,694 A | 10/1997 | Boser et al. | |
| 5,760,341 A | 6/1998 | Laske et al. | |
| 6,400,992 B1 * | 6/2002 | Borgersen et al. | 607/122 |
| 6,785,576 B2 | 8/2004 | Verness | |
| 7,108,549 B2 | 9/2006 | Lyu et al. | |
| 7,168,165 B2 * | 1/2007 | Calzada et al. | 29/860 |
| 7,184,839 B2 | 2/2007 | Clemens et al. | |
| 7,225,035 B2 * | 5/2007 | Brabec et al. | 607/122 |
| 2002/0099430 A1 | 7/2002 | Verness | |
| 2002/0183824 A1 | 12/2002 | Borgersen et al. | |
| 2005/0080471 A1 * | 4/2005 | Chitre et al. | 607/122 |
| 2009/0082655 A1 | 3/2009 | Seifert et al. | |

FOREIGN PATENT DOCUMENTS

WO WO 2011/146168 A1 11/2011

OTHER PUBLICATIONS (PCT/US2013/021171) PCT Notification of Transmittal of the International Search Report and the Written Opinion of the International Searching Authority.

* cited by examiner

*Primary Examiner* — Carl H Layno
*Assistant Examiner* — Paula J Stice
(74) *Attorney, Agent, or Firm* — Reed A. Duthler

(57) ABSTRACT

An integrated bipolar implantable medical electrical lead, which may be employed by a cardiac defibrillator, has a single low voltage electrode and a single high voltage electrode and employs a relatively robust and fail-safe configuration of three conductors. Each of the three conductors extends within an individual lumen of a tri-lumen insulative body of the lead. First and second conductors of the three connect, in parallel, the low voltage electrode to a first contact of a connector terminal assembly of the lead, and a third conductor of the three connects the high voltage electrode to a second and a third contact of the connector terminal assembly. A configuration of the third conductor differs from that of the first and second conductors in order to make the third conductor more susceptible to fracture, relative to the first and second conductors, after many years of chronic implant under extreme loading conditions.

11 Claims, 4 Drawing Sheets

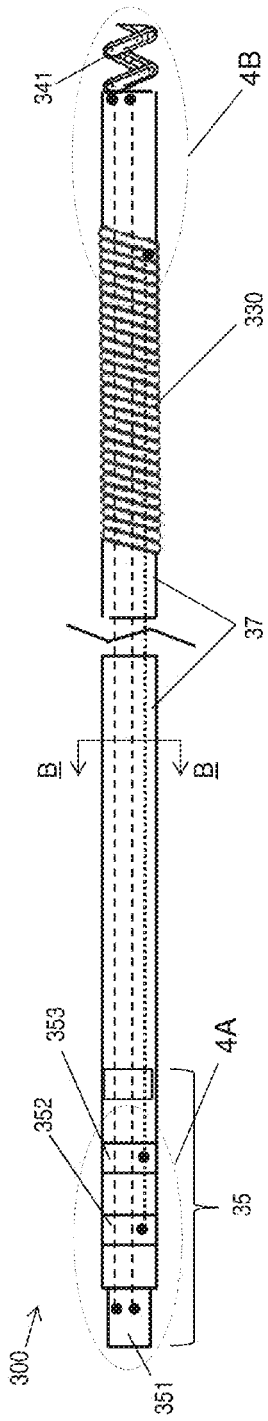
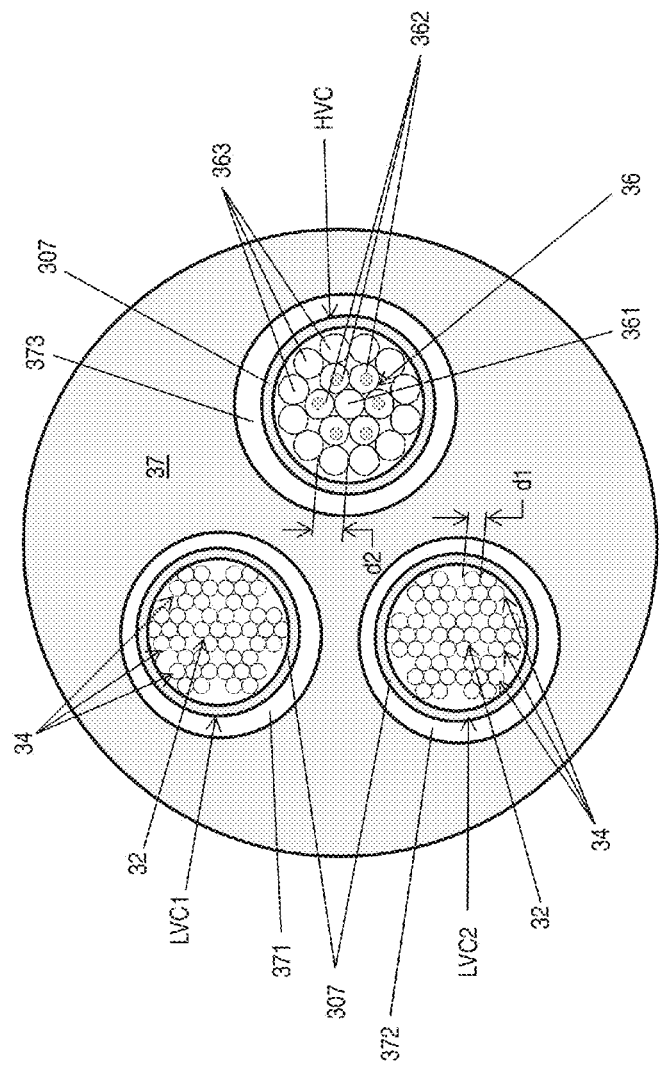
FIGURE 3A
FIGURE 3B

FAIL-SAFE IMPLANTABLE MEDICAL ELECTRICAL LEAD

FIELD OF THE DISCLOSURE

The present invention pertains to implantable medical electrical leads for cardiac defibrillation, and, more specifically to fail-safe configurations thereof.

BACKGROUND

Implantable cardiac defibrillators (ICD's) are designed to detect cardiac fibrillation and, in response to the detection, to deliver high voltage shock therapy in order to terminate the fibrillation. FIG. 1 is a schematic showing a typical subcutaneous pectoral placement of an ICD 100 in a patient 102, wherein a hermetically sealed and biocompatible canister 104 of ICD 100 houses circuitry to enable detection and therapy delivery via an elongate electrical lead 106, which is coupled to the circuitry and extends distally from canister 104, through the venous system 110 and into the heart 108 of patient 102, for example, the right ventricle RV. Those skilled in the art understand that implantable medical electrical leads, like lead 106, typically include pacing, sensing and defibrillation electrodes. The electrodes of lead 106 are coupled to the ICD circuitry via a connector terminal assembly that terminates elongate insulated conductors of the electrodes, at a proximal end of lead 106; the connector terminal assembly is plugged into a connector module 105, which is mounted on canister 104, to make electrical contact with the contained ICD circuitry via hermetically sealed feedthroughs. Canister 104, for example, formed from a Titanium alloy, is typically employed as a high voltage electrode in conjunction with a high voltage electrode of lead 106 to establish an effective shocking vector for cardiac defibrillation.

Those skilled in the art are familiar with the repetitive stresses of cyclic loading to which implanted medical electrical leads are subjected, and that these stresses make the elongate conductors of implantable medical electrical leads susceptible to fracture after many years of chronic implantation. In certain instances, such as when the wire filars of a lead conductor that completes a sensing circuit for an ICD become fractured, intermittent contact at the fracture site may produce signals that mimic cardiac fibrillation signals and are erroneously detected as such, leading to subsequent delivery of unnecessary high voltage shock therapy. Thus, a variety of conductor configurations and lead body designs have been developed to increase fracture resistance and/or to address such fractures with redundant conductors. Nevertheless, there is still a need for more robust and fail-safe configurations of conductors in implantable medical electrical leads employed by ICD's.

SUMMARY

Embodiments of an implantable medical electrical lead, which may be employed by a cardiac defibrillator, include relatively robust and fail-safe configurations of conductors. In preferred embodiments, the lead includes a single low voltage electrode, a single high voltage electrode, and a tri-lumen insulative lead body, wherein first and second conductors of the lead, which extend in corresponding first and second lumens of the lead body connect, in parallel, the low voltage electrode to a first contact of a connector terminal assembly of the lead, while a third conductor of the lead, which extends in a third lumen of the lead body, connects the high voltage electrode to a second contact and to a third contact of the connector terminal assembly.

According to some embodiments, the first and second conductors connecting the low voltage electrode each include a first type of central wire bundle made up of a plurality of wire filars, each wire filar of the first type having a first diameter; and the third conductor connecting the high voltage electrode includes a second type of central wire bundle made up of a plurality of wire filars, each wire filar of the second type having a second diameter that is greater than the first diameter. Some or all of the wire filars of the third conductor may each be formed as a drawn filled tube (DFT) type wire, wherein a conductive material that fills the tube of each wire filar is more conductive than that which forms the tube. Furthermore, each of the first and second conductors may further include a plurality of perimeter wire bundles, which are wrapped around the corresponding central wire bundle, while the third conductor does not. According to some preferred embodiments, the first and second conductors are more flex-failure resistant than the third conductor, for example, being formed of wire filars that are greater in number and of a smaller diameter than those of which the third conductor is formed; the wire filars of each of the first and second conductors are preferably arranged in a 7×7 cable configuration, while the wire filars of the third conductor are preferably arranged in a 1×19 cable configuration.

BRIEF DESCRIPTION OF THE DRAWINGS

The following drawings are illustrative of particular embodiments of the present invention and therefore do not limit the scope of the invention. The drawings are not to scale (unless so stated) and are intended for use in conjunction with the explanations in the following detailed description. Embodiments will hereinafter be described in conjunction with the appended drawings wherein like numerals/letters denote like elements, and:

FIG. 3A is a plan view of an implantable medical electrical lead, according to some embodiments of the present invention;

FIG. 3B is a section view through section line B-B of FIG. 3A, according to some embodiments;

DETAILED DESCRIPTION

The following detailed description is exemplary in nature and is not intended to limit the scope, applicability, or configuration of the invention in any way. Rather, the following description provides practical examples, and those skilled in the art will recognize that some of the examples may have suitable alternatives.

Figure 1:
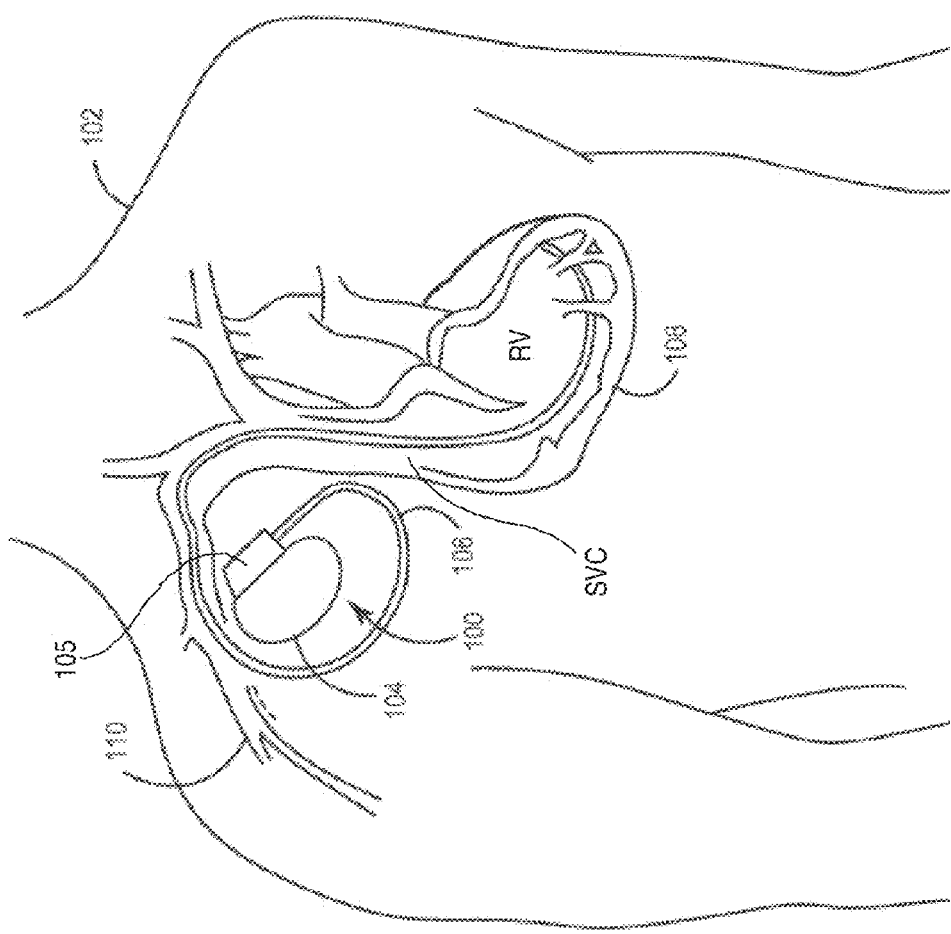
FIG. 1 is a schematic showing a typical placement of an implanted cardioverter defibrillator.
Figure 2:
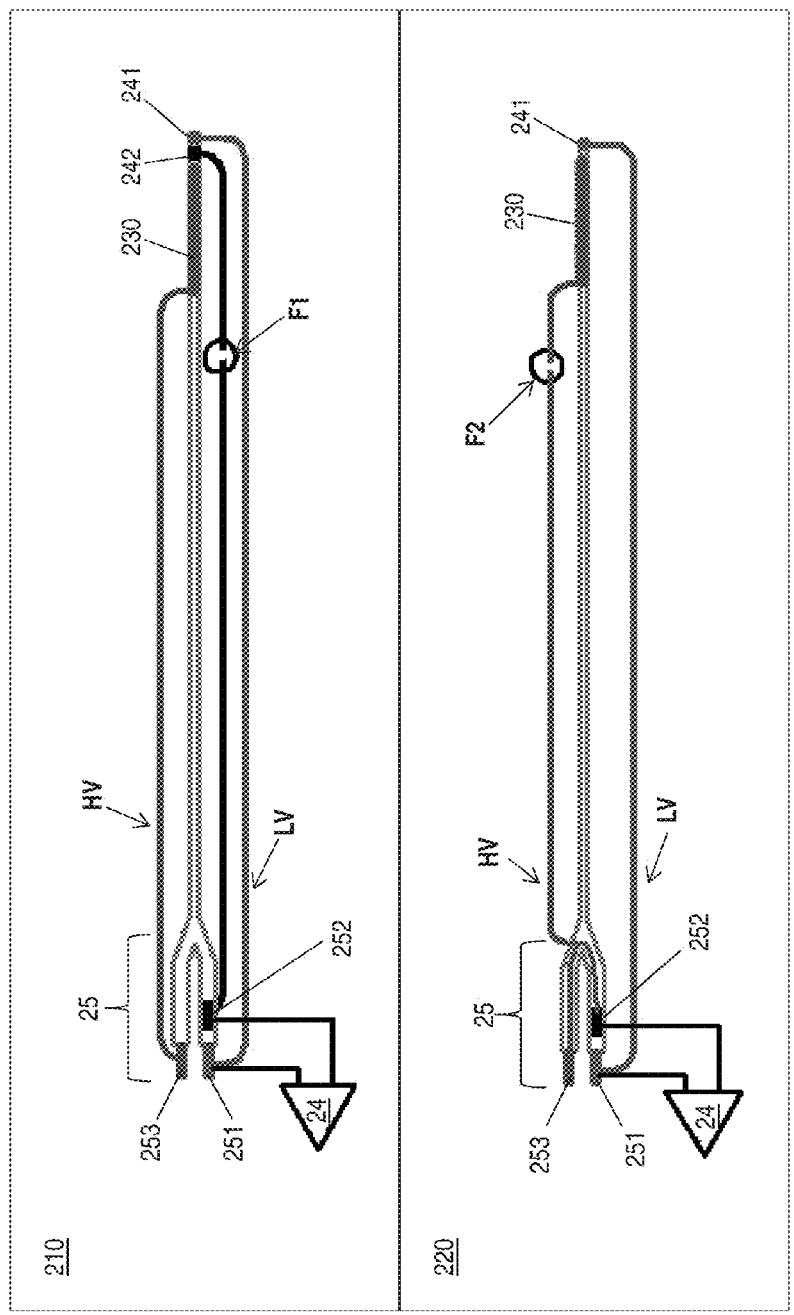
FIG. 2 is a schematic comparing a true bipolar lead configuration to an integrated bipolar lead configuration.

FIG. 2 is a schematic comparing a typical true bipolar (TB) lead configuration 210 to a typical integrated bipolar (IB) lead configuration 220, either of which may be employed by ICD 100 for lead 106 of FIG. 1. FIG. 2 illustrates TB lead configuration 210 including a pair of low voltage (LV) electrodes 241, 242, which are employed by a sense circuit 24, for example, of the aforementioned ICD circuitry, for the purpose of detecting cardiac fibrillation. FIG. 2 further illustrates IB lead configuration 220 including only LV electrode 241, which is employed, in conjunction with a high voltage (HV) electrode 230, by sense circuit 24 for the purpose of detecting cardiac fibrillation. In both configurations 210, 220, HV electrode 230 is located relative to LV electrode 241 for implant in the right ventricle RV (FIG. 1), so as to be employed, for example, in conjunction with canister 104 and/or with another defibrillation electrode (of the same or a separate lead), for example, implanted in the superior vena cava SVC, to deliver HV shock therapy upon the detection of fibrillation.

As alluded to above, in the Background description of FIG. 1, a connector terminal assembly 25 terminates elongate conductors of each lead configuration 210, 220, which conductors are shown schematically in FIG. 2 extending between corresponding electrodes and connector contacts to form an LV sensing circuit LV and an HV therapy delivery circuit HV of each configuration 210, 220. With further reference to FIG. 2, in configuration 210, a separate conductor connects each of electrodes 230, 241, 242 to a corresponding connector contact 253, 251, 252 of connector terminal assembly 25; and, in configuration 220, a single conductor connects electrode 241 to connector contact 251, while a separate single conductor connects electrode 230 to both of contacts 252 and 253. Thus, HV electrode 230, in the absence of LV electrode 242, is employed for both sensing and HV therapy delivery in IB lead configuration 220, and the conductor connecting electrode 230 is an element of both circuits HV and LV. Although the independent sense circuit of TB configuration 210 (employing electrodes 241, 242) may provide superior sensing for more accurate detection cardiac events, in some instances, IB configuration 220 has been found to provide adequate sensing performance; thus, both configurations 210, 220 are routinely employed, depending upon the preference of the implanting physician, and both include connector terminal assemblies compatible with standard ICD's (i.e. for plugging into connector module 105, FIG. 1).

FIG. 2 further illustrates a potential fracture F1, F2 of a conductor in each of configurations 210, 220, which may be induced by extreme loading conditions extending over many years of a chronic implant. Fractures F1 and F2 may not likely result in 'clean' separation of broken conductor ends, due to state of the art lead construction, for example, employing relatively tight fitting insulative jackets around conductors and/or multi-filar cable configurations; thus, lead motion, for example, caused by the pumping motion of the patient's heart and/or upper body movement of the patient, in conjunction with fractures F1 and F2, can cause the broken conductor ends to intermittently connect and disconnect resulting in impedance fluctuations that sense circuit 24 may mistake for cardiac fibrillation. This mistaken detection of cardiac fibrillation can lead to the delivery of an inappropriate/unnecessary HV shock. With further reference to FIG. 2, the delivery of the unnecessary HV shock in the TB lead configuration 210 may be repeated multiple times before fracture F1 is addressed; but, during the delivery of the first unnecessary HV shock, subsequent to facture F2 in the IB lead configuration 220, any 'touch points' of intermittent connections at the site of fracture F2 will likely 'blow open' like a fuse to disable circuit HV and thereby prevent any additional inappropriate HV shocks. Although the conductor of circuit LV in IB lead configuration 220 may be just as likely, or almost as likely to fracture as the conductor of circuit HV thereof, the probability of fracture of circuit HV in TB lead configuration 210 may be lower than that in IB lead configuration 220, due to the greater number of LV conductors employed in the TB lead configuration, if all other design and construction aspects of the two configurations are similar. Thus, in view of the benefit of a failure mechanism that disables circuit HV, thereby preventing multiple inappropriate shocks, IB lead configuration 220 may be more fail-safe than TB lead configuration 210.

FIG. 3A is a plan view of an IB implantable medical electrical lead 300 for use with an ICD, according to some embodiments of the present invention; and FIG. 3B is a section view through section line B-B of FIG. 3A, according to some embodiments. FIG. 3A illustrates lead 300 including an elongate insulative body 37, a single LV electrode 341, a single HV electrode 330, and a connector terminal assembly 35, which includes a first contact 351, a second contact 352, and a third contact 353. According to some embodiments, connector terminal assembly 35 further includes a fourth, inactive contact employed solely to conform with the form factor of the DF-4 industry standard.

Dashed lines in FIG. 3A illustrate a pair of individual conductors connecting, in parallel, LV electrode 341 to first contact 351 of connector terminal assembly 35. With reference to FIG. 3B, a first conductor LVC1 of the pair extends in a first lumen 371 of insulative lead body 37, between LV electrode 341 and first contact 351, and second conductor LVC2 of the pair extends in a second lumen 372 of insulative lead body 37, between LV electrode 341 and first contact 351. Lead body 37 preferably includes only three lumens and a third conductor HVC extends within a third lumen 373 thereof to connect HV electrode 330 to both contacts 352 and 353, as illustrated by a dotted line in FIG. 3A. (Exemplary junctions between each conductor LVC1, LVC2, HVC and corresponding electrodes and connector assembly contacts will be described below.) Lead body 37 may be formed, according to methods known in the art, from medical implant grade insulative materials known in the art of implantable medical electrical lead construction, for example, silicone rubber and/or polyurethane, and/or silicone-urethane copolymer. According to some preferred embodiments, lead body 37 is formed from a silicone tri-lumen tubing having a polyurethane overlay extending about portions thereof.

According to preferred embodiments of the present invention, as illustrated in FIGS. 3A-B, the typical IB lead configuration, for example, configuration 220 shown schematically in FIG. 2, is made more robust and fail-safe by employing a tri-lumen insulative lead body (i.e. lead body 37). The tri-lumen configuration of lead body 37 not only makes the connection between LV electrode 341 and connector contact 351 more robust, by providing an additional lumen for the addition of a redundant conductor (i.e. one of the pair of conductors LVC1, LVC2), but also reduces the probability of lead 300 having a preferred bending axis that could contribute to consistent and repeated stressing of one of conductors LVC1, LVC2, HVC more than the others, during an extended period of chronic implant. Furthermore, the different configuration of conductor HVC, compared to conductors LVC1, LVC2, as described below, may further increase the likelihood of conductor HVC being the first to fracture under chronic and extreme loading conditions, resulting in a fail-safe failure mechanism for lead 300 that avoids the above-described scenario of delivering multiple unnecessary/inappropriate HV shocks.

FIG. 3B illustrates each of conductors LVC1, LVC2 being formed of a plurality of cabled wire filars of a different type and configuration that that which is employed by third conductor HVC. Each conductor LVC1, LVC2, HVC is shown including an optional insulative jacket 307, for example, that may be formed from a fluoropolymer material such as ETFE or PTFE. According to the illustrated embodiment, the wire filars of conductors LVC1, LVC2 are more numerous than those of conductor HVC, and each wire filar of conductors LVC1, LVC2 has a diameter d1 that is smaller than a diameter d2 of each wire filar of conductor HVC. For example, diameter d1 of each wire filar of each of conductors LVC1, LVC2 is between approximately 0.0007 inch and approximately 0.0009 inch, and diameter d2 of each wire filar of conductor HVC is between approximately 0.0011 inch and approximately 0.0013 inch. Thus, it may be inferred that conductors LVC1, LVC2 may be more flex-failure resistant than conductor HVC, which has a fewer number of wire filars that are of a larger diameter, so that conductor HVC is more likely to fracture before either of conductors LVC1, LVC2, under extreme and chronic cyclic loading conditions. In addition, according to some embodiments, which are described below, the incorporation of reduced-resistance wire filars in third conductor HVC, which is desirable for more efficient delivery of HV shock therapy, may further weaken conductor HVC, relative to conductors LVC1, LVC2, to achieve the above-described fail-safe failure mechanism.

With further reference to FIG. 3B, conductors LVC1, LVC2 each include a 1×7 central wire bundle 32 and six more 1×7 perimeter bundles 34 that are wrapped around central wire bundle 32 according to a 7×7 cable configuration that is known in the art and described in commonly assigned U.S. Pat. No. 5,760,341. Each wire filar of conductors LVC1, LVC2 are preferably formed from MP35N alloy, which is known to those skilled in the art. FIG. 3B further illustrates third conductor HVC including a 1×7 central wire bundle 36 in which a core wire 361 is solid, for example, MP35N alloy, while each of six perimeter wire filars 363 is preferably a drawn filled tube (DFT) type wire, wherein a conductive material that fills (i.e. silver) the tube of each wire filar is more conductive than the conductive material which forms the tube (i.e. MP35N alloy). Incorporation of this DFT type wire, which is known in the art, reduces the resistance of third conductor HVC for a more efficient delivery of HV shock therapy. According to an exemplary embodiment, filars 362 are approximately 75% MP35N alloy, by volume, and approximately 25% silver, by volume. Conductor HVC further includes individual outer perimeter wire filars 363 (i.e. MP35N alloy) wrapped about central wire bundle 36, such that all the wire filars of are arranged in what is known to those skilled in the art as a 1×19 cable configuration. Although core wire 361 and outer perimeter wire filars 363 of conductor HVC are illustrated as solid wires, according to alternate embodiments, some or all of core wire 361 and outer perimeter wires 363 may be DFT type wire, like filars 362.

Figure 4A:
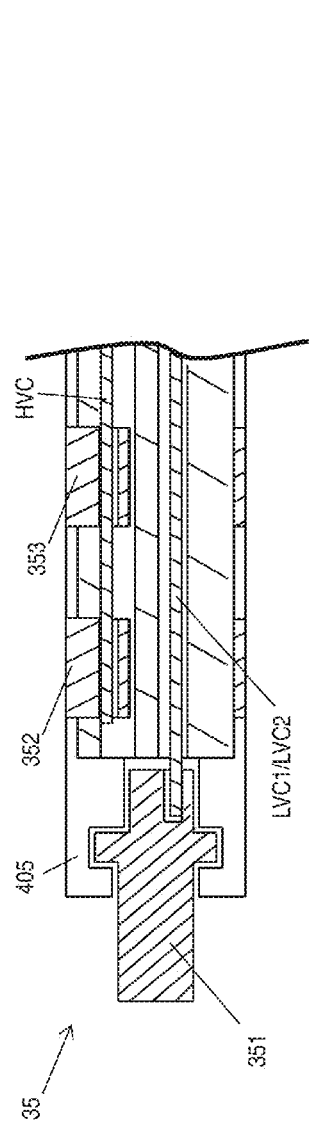
FIGS. 4A-B are longitudinal section views of a portion of a connector terminal assembly and a distal portion, respectively, of the lead shown in FIG. 3A, according to some exemplary embodiments.
Figure 4B:
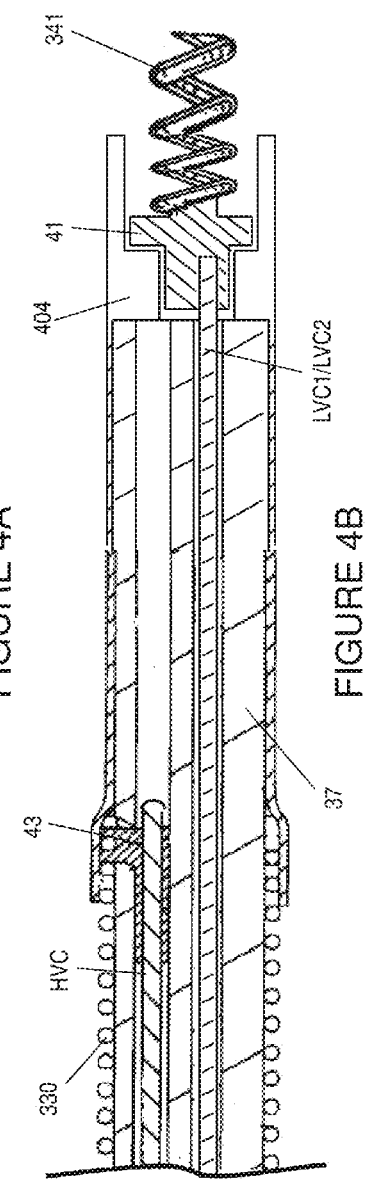
Figure 4C:
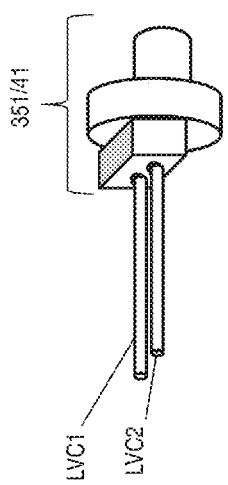
FIG. 4C is a perspective view of a junction that may be employed for conductors of the lead, according to some exemplary embodiments.

Turning now to FIGS. 4A-C, exemplary junctions between each conductor LVC1, LVC2, HVC and corresponding electrodes and connector assembly contacts will be described. A variety of alternate configurations and methods for forming such junctions are known in the art, so the scope of the present invention should not be limited by the following description. FIGS. 4A-B are longitudinal section views of a portion of connector terminal assembly 35 and a distal portion, respectively, of lead 300, according to some embodiments; and FIG. 4C is a perspective view of a junction that may be employed for conductors LVC1, LVC2, according to some embodiments. FIG. 4A illustrates a proximal portion of third conductor HVC coupled within internal eyelet/sleeve portions of connector contacts 352 and 353, for example, via a crimp joint formed according to methods known in the art; and FIG. 4B illustrates a distal portion of third conductor HVC coupled, for example, by crimping, within a sleeve portion of a component 43 to which HV electrode 330 is also coupled, for example, by laser welding. Component 43 may be configured, and the junctions of electrode 330 and conductor HVC with component 43 may be formed, according to the teaching of commonly assigned U.S. Pat. No. 5,676,694. FIG. 4A further illustrates a proximal end of one of first conductor LVC1 and second conductor LVC2 coupled, for example, by crimping, to first contact 351; and FIG. 4B further illustrates a distal end of one of first conductor LVC1 and second conductor LVC2 coupled, for example, by crimping, to an electrode stud component 41 to which LV electrode 342 is also coupled, for example, by laser welding. With reference to FIG. 4C, according to the illustrated embodiment, connector contact 351 and electrode stud component 41 may have a similar configuration to accommodate the coupling, by crimp joint, of both first and second conductors LVC1, LVC2 thereto, and to accommodate a mechanical interlock with a corresponding insulative retainer 405, 404 (FIGS. 4A-B). Retainers 405, 404 may be formed from a relatively rigid implantable medical grade polyurethane, for example, having a hardness of 75 D. FIG. 4C illustrates the end of each of first and second conductors LVC1, LVC2 inserted in to a bore of a corresponding pair of bores that may be formed in one or both of connector contact 351 and electrode stud component 41; alternately a single bore may be formed to receive both conductors LVC1, LVC2 for the junction therewith. Connector contact 351 is preferably formed from a medical grade stainless steel, for example, 316L; and, since a 90/10 platinum iridium alloy is the preferred material for LV electrode 341, electrode stud component 41 is, preferably, also formed from the 90/10 platinum iridium alloy for compatibility of laser welding LV electrode 341 thereto.

It should be noted that, although FIGS. 3A and 4A illustrate connector terminal assembly 35 constructed in-line with lead body 37 (i.e. conforming to the DF-4 industry standard), embodiments of the present invention may alternately incorporate a bifurcated construction, for example, like that shown schematically for IB lead configuration in FIG. 2, which includes a LV connector leg (i.e. conforming to the IS-1 industry standard) and a HV connector leg (i.e. conforming to the DF-1 industry standard). Furthermore, although FIGS. 3A and 4B illustrate LV electrode 341 formed as a helical, screw-in fixation type electrode, a configuration that is known in the art, according to alternate embodiments, electrode 341 may be formed as a dome-shaped tip electrode in conjunction with insulative tines for fixation, a configuration that is also known in the art.

In the foregoing detailed description, the invention has been described with reference to specific embodiments. However, it may be appreciated that various modifications and changes can be made without departing from the scope of the invention as set forth in the appended claims. For example, alternate embodiments can encompass alternative numbers of secondary windings to those illustrated.

The invention claimed is:

1. An integrated bipolar implantable medical electrical lead comprising a single low voltage electrode, a single high voltage electrode, and a connector terminal assembly including a first contact, corresponding to the low voltage electrode, and second and third contacts, both corresponding to the high voltage electrode; and the lead further comprising:

a tri-lumen insulative lead body extending between the electrodes and the connector terminal assembly;

a pair of individual conductors connecting, in parallel, the low voltage electrode to the first contact of the connector terminal assembly, a first conductor of the pair of individual conductors extending within a first lumen of the tri-lumen lead body, and a second conductor of the pair extending within a second lumen of the lead body; and a third conductor connecting the high voltage electrode to the second contact and to the third contact of the connector terminal assembly, the third conductor extending within a third lumen of the tri-lumen lead body;

wherein the first and second conductors each comprise a central wire bundle of a first type made up of a plurality of wire filars, each wire filar of the first type having a first diameter; and the third conductor comprises a central wire bundle of a second type made up of a plurality of wire filars, each wire filar of the second type having a second diameter, the second diameter being greater than the first diameter.

2. The lead of claim 1, wherein the third conductor further comprises a plurality of individual perimeter wire filars wrapped around the central wire bundle thereof such that all the wire filars of the third conductor are arranged in a 1×19 cable configuration.

3. The lead of claim 2, wherein some or all of the wire filars of the third conductor each comprise a tube formed of a first conductive material that is filled with a second conductive material, the second conductive material having a greater conductivity than the first conductive material.

4. The lead of claim 1, wherein some or all of the wire filars of the central wire bundle of the third conductor each comprise a tube formed of a first conductive material that is filled with a second conductive material, the second conductive material having a greater conductivity than the first conductive material.

5. The lead of claim 4, wherein the third conductor further comprises a plurality of individual perimeter wire filars wrapped around the central wire bundle thereof such that all the wire filars of the third conductor are arranged in a 1×19 cable configuration.

6. The lead of claim 1, wherein the first and second conductors each further comprise a plurality of perimeter wire bundles, each perimeter wire bundle being wrapped around a corresponding central wire bundle.

7. The lead of claim 6, wherein the third conductor further comprises a plurality of individual perimeter wire filars wrapped around the central wire bundle thereof such that all the wire filars of the third conductor are arranged in a 1×19 cable configuration.

8. The lead of claim 6, wherein some or all of the wire filars of the central wire bundle of the third conductor each comprise a tube formed of a first conductive material that is filled with a second conductive material, the second conductive material having a greater conductivity than the first conductive material.

9. The lead of claim 6, wherein:
a number of the plurality of perimeter wire bundles is seven;
the wire filars of each of the central wire bundle and the perimeter wire bundles of the first and second conductors are arranged in a 1×7 cable configuration; and
all of the wire filars of each of the first and second conductors are arranged in a 7×7 cable configuration.

10. The lead of claim 9, wherein the third conductor further comprises perimeter wire filars wrapped around the central wire bundle thereof such that all the wire filars of the third conductor are arranged in a 1×19 cable configuration.

11. The lead of claim 10, wherein some or all of the wire filars of the third conductor each comprise a tube formed of a first conductive material that is filled with a second conductive material, the second conductive material having a greater conductivity than the first conductive material.

* * * * *